US00PP12994P2

(12) United States Plant Patent
Zary

(10) Patent No.: US PP12,994 P2
(45) Date of Patent: Sep. 24, 2002

(54) MINIATURE ROSE PLANT NAMED 'JACRENIM'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 53 days.

(21) Appl. No.: 09/696,345

(22) Filed: Oct. 24, 2000

(51) Int. Cl.[7] ..... A01H 5/00
(52) U.S. Cl. ..... Plt./129
(58) Field of Search ..... Plt./122, 129, 150, Plt./151

*Primary Examiner*—Howard J. Locker
(74) *Attorney, Agent, or Firm*—Klarquist Sparkman, LLP

(57) ABSTRACT

Miniature rose plant characterized by its bright red flowers; small, narrow, dark, green, glossy foliage; compact well-branched habit; many small prickles on stems; resistance to powdery mildew and rust; and ease of propagation from softwood cuttings.

1 Drawing Sheet

1

The present invention relates to a new and distinct variety of rose plant of the miniature class which was originated by me by crossing two unnamed varieties.

The primary objective of this breeding was to produce a new rose variety having the deep red flower color and dark glossy foliage of the female parent combined with the compact, rounded, well-branched habit of the male parent. The objective was substantially achieved, along with other desirable improvements, as evidenced by the following unique combination of characteristics that are outstanding in the new variety and that distinguish it from its parents, as well as from all other varieties of which I am aware:

1. Bright red flower color;
2. Small, narrow, dark green glossy foliage;
3. Compact, well-branched plant habit;
4. Many small prickles on stems;
5. Resistance to powdery mildew and rust; and
6. Ease of propagation from softwood cuttings.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (Unnamed seedling× 'MACminmo' (U.S. Plant Pat. No. 7,319)).

*Pollen parent.*—Unnamed seedling (Unnamed seedling×'JACup' (not patented)).

Classification:

*Botanical.*—*Rosa hybrida.*

*Commercial.*—Miniature.

2

FLOWER

Observations made from specimens grown in a garden environment at Somis, Calif. in January 1999 through July 2000.

Blooming habit: Continuous.

Bud:

*Size.*—½"×⅝" long when the petals start to unfurl.

*Form.*—The bud form is long, pointed ovoid.

*Color.*—When sepals first divide, bud color is Red Group 46A. When half blown, the upper sides of the petals are Red Group 46B; and the lower sides of the petals are Red Group 53B.

*Sepals.*—Color: Green Group 138C, often with Greyed-Purple Group 183C in areas exposed to bright sunlight. Surface texture: Covered in fine hairs. There are three normally to heavily appendaged sepals. There are two unappendaged sepals with hairy edges.

*Receptacle.*—Color: Green Group 137B, sometimes with Greyed-Purple Group 183B in areas exposed to bright sunlight. Shape: Funnel. Size: Small (about ¼"×¼"). Surface: Smooth.

*Peduncle.*—Length: Short (about 1¼"). Surface: Glandular. Color: Green Group 137D, often with areas of Greyed-Purple Group 183B in areas exposed to bright light. Strength: Stiff, erect.

Bloom:

*Size.*—Small. Average open size is 2."

*Borne.*—Several together in pyramidal clusters of three to seven blooms.

*Stems.*—Strength Strong. Average length is about 8"–10."

*Form.*—When first open: High centered. Permanence: Flattens; all petals curl with some quilling.

*Petalage.*—Number of petals under normal conditions: 20.

*Color.*—The upper sides of the petals are Red Group 46B. The reverse sides of the petals are Red Group 53B. The base of each petal has a small 3/16×⅛" Yellow Group 11C spot on the upper surface and lower surface of the petals. The major color on the upper side is Red Group 46B.

*Variegations.*—Occasional White Group 155D streak on the guard petals and on some interior petals.

*Discoloration.*—The general tonality at the end of the first day: No change. At the end of the third day: No change.

*Fragrance.*—None.

Petals:

*Texture.*—Thick; leathery.

*Shape.*—Round to deltoid.

*Form.*—Tips slightly recurved; edges slightly quilled.

*Arrangement.*—Imbricated. No petaloids.

*Persistance.*—Petals drop off cleanly before drying.

*Lastingness.*—On the plant: Fair (about 5 to 6 days). As a cut flower: Fair (about 6 to 7 days).

Reproductive parts:

*Anthers.*—Size: Small. Quantity: Many. Color: Yellow-Orange Group 22D. Arrangement: Regular around styles.

*Filaments.*—Color: Red Group 46A.

*Pollen.*—Color: Yellow-Orange Group 22A.

*Styles.*—Color: Red Group 53A.

*Stigmas.*—Color: Yellow-White Group 158C.

Plant:

*Form.*—Bush.

*Growth.*—Vigorous; upright; branching; compact. At maturity, height is 2½ feet and width is 2 feet after one year of growth.

Foliage: Number of leaflets on normal mid-stem leaves: is 5 or 7.

*Size.*—Small (3"–3½" long×1½" wide).

*Quantity.*—Normal.

*Color.*—New foliage: Upper and lower surfaces: Greyed Red Group 178A. Old foliage: Upper surface: Green Group 136A. Lower surface: Green Group 138A.

Leaflets:

*Shape.*—Pointed oval.

*Texture.*—Leathery; glossy.

*Edge.*—Serrated.

*Serration.*—Single; small.

*Petiole rachis.*—Color: Upper: Greyed-Purple Group 183B. Lower: Green Group 138C.

*Petiole underside.*—Smooth with occasional prickles.

*Stipules.*—Long; (about ⅝"); narrow; serrated; bearded.

*Disease resistance.*—Resistant to rust and mildew under normal growing conditions. Susceptible to blackspot.

Wood:

*New wood.*—Color: Greyed-Red Group 178A. Bark: Smooth.

*Old wood.*—Color: Green Group 137A. Bark: Smooth.

Prickles:

*Quantity.*—On main canes from base: Many. On laterals from main canes: Many.

*Form.*—Medium; hooked slightly downward.

*Color when young.*—Greyed-Purple Group 183A.

*Color when mature.*—Greyed-Orange Group 166A.

Small prickles:

*Quantity.*—On main stalks: Many. On laterals: Many.

*Color.*—Young: Greyed-Purple Group 183A; Old: Greyed-Orange Group 166A.

I claim:

1. A new and distinct variety of rose plant of the miniature class, substantially as herein shown and described, characterized particularly by its bright red flowers; small, narrow, dark, green, glossy foliage; compact well-branched habit; many small prickles on stems; resistance to powdery mildew and rust; and ease of propagation from softwood cuttings.

* * * * *

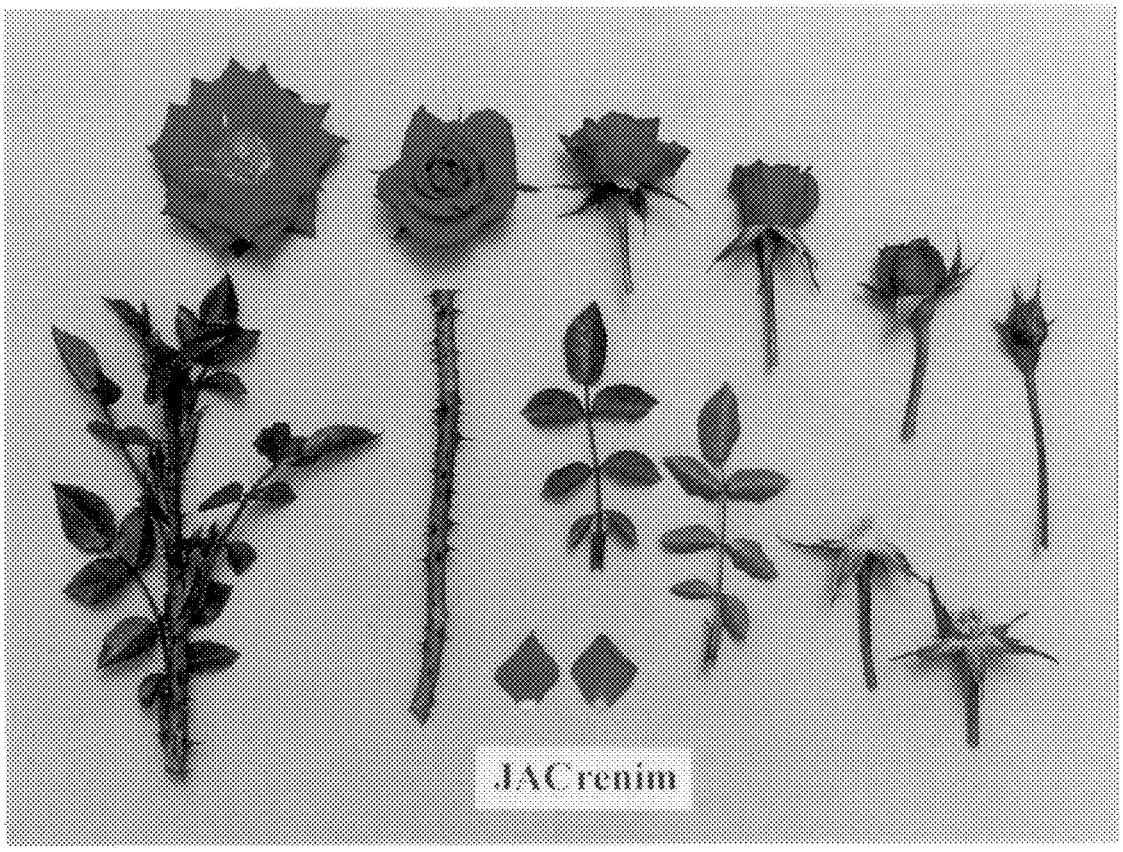
JACrenim